(12) United States Patent
Christensen (10) Patent No.: US 9,524,480 B2
(45) Date of Patent: Dec. 20, 2016

(54) HYGIENE BEHAVIOUR SUPPORT SYSTEM WITH SENSORS AND AN AUTOMATIC DOOR

(71) Applicant: BERENDSEN A/S, Ørestad, Copenhagen S (DK)

(72) Inventor: Jarl Christensen, Højbjerg (DK)

(73) Assignee: BERENDSEN A/S, Ørestad, Copenhagen S (DK)

( * ) Notice: Subject to any disclaimer, the term of this patent is extended or adjusted under 35 U.S.C. 154(b) by 61 days.

(21) Appl. No.: 14/421,764

(22) PCT Filed: Aug. 14, 2013

(86) PCT No.: PCT/EP2013/067002
§ 371 (c)(1),
(2) Date: Feb. 13, 2015

(87) PCT Pub. No.: WO2014/027030
PCT Pub. Date: Feb. 20, 2014

(65) Prior Publication Data
US 2015/0213707 A1 Jul. 30, 2015

(30) Foreign Application Priority Data
Aug. 14, 2012 (EP) .................................. 12180442

(51) Int. Cl.
*G08B 21/00* (2006.01)
*G06Q 10/06* (2012.01)
(Continued)

(52) U.S. Cl.
CPC ......... *G06Q 10/06393* (2013.01); *E05F 15/74* (2015.01); *G06F 19/327* (2013.01);
(Continued)

(58) Field of Classification Search
CPC ... E05F 15/74; E05F 2015/765; G06F 19/327; G06Q 10/06395; G06Q 10/06393; G08B 21/245
(Continued)

(56) References Cited

U.S. PATENT DOCUMENTS

| 5,808,553 A | 9/1998 | Cunningham |
| 2003/0030562 A1* | 2/2003 | Lane .................... G08B 21/245 340/573.4 |

(Continued)

FOREIGN PATENT DOCUMENTS

| WO | WO 02/059701 | 8/2002 |
| WO | WO 2005/040984 | 5/2005 |
| WO | WO 2011/032564 | 3/2011 |

OTHER PUBLICATIONS

International Search Report for PCT/EP2013/067002 mailed Feb. 24, 2014, 8 pages.
(Continued)

*Primary Examiner* — Mark Rushing
(74) *Attorney, Agent, or Firm* — Nixon & Vanderhye P.C.

(57) ABSTRACT

The present invention relates to a hygiene behaviour support system for enhancing a person's hand hygiene after a toilet visit. Visual LED indicators are provided on a water tap, soap dispenser, paper dispenser and disinfectant dispender to attract the attention of the user to the respective item. Sensors on the items activate the dispensers and register completion of each task, in order to activate the next indicator on the next item, thereby sequentially guiding the user through a complete hygiene procedure. The disinfectant dispenser is connected with the closing mechanism of the door, so that only after the disinfectant is sensed to have been dispensed, the door will open.

27 Claims, 6 Drawing Sheets

(51) Int. Cl.
   *G06Q 50/22* (2012.01)
   *G08B 21/24* (2006.01)
   *G06F 19/00* (2011.01)
   *G06Q 10/00* (2012.01)
   *G06Q 50/10* (2012.01)
   *E05F 15/74* (2015.01)
   *E05F 15/73* (2015.01)

(52) U.S. Cl.
   CPC ............ *G06Q 10/00* (2013.01); *G06Q 10/06* (2013.01); *G06Q 10/06395* (2013.01); *G06Q 50/10* (2013.01); *G06Q 50/22* (2013.01); *G08B 21/245* (2013.01); *E05F 2015/765* (2015.01)

(58) Field of Classification Search
   USPC ....................................................... 340/573.1
   See application file for complete search history.

(56) References Cited

U.S. PATENT DOCUMENTS

| | | | |
|---|---|---|---|
| 2004/0090333 A1* | 5/2004 | Wildman | G06F 19/3418 340/573.1 |
| 2008/0131332 A1* | 6/2008 | Nguyen | A61L 2/24 422/119 |
| 2009/0051545 A1* | 2/2009 | Koblasz | G08B 21/245 340/573.1 |
| 2012/0212344 A1* | 8/2012 | Forsberg | G08B 3/10 340/573.1 |

OTHER PUBLICATIONS

Written Opinion of the ISA for PCT/EP2013/067002 mailed Feb. 24, 2014, 11 pages.

* cited by examiner

HYGIENE BEHAVIOUR SUPPORT SYSTEM WITH SENSORS AND AN AUTOMATIC DOOR

This application is the U.S. national phase of International Application No. PCT/EP2013/067002 filed 14 Aug. 2013 which designated the U.S. and claims priority to EP Patent Application No. 12180442.1 filed 14 Aug. 2012, the entire contents of each of which are hereby incorporated by reference.

FIELD OF THE INVENTION

The present invention relates to a hygiene behaviour support system for enhancing a lavatory user's hand hygiene after a toilet visit. The system comprises a lavatory comprising a toilet having a first sensor, a soap dispenser having a second sensor, a sink having a water tap, the water tap having a third sensor, a paper dispenser having a fourth sensor, and a disinfectant dispenser having a fifth sensor, and a door through which a user can enter or leave the lavatory, the door having a closing mechanism.

BACKGROUND ART

Surveys show that 10 percent of all hospitalised patients acquire an infection due to inadequate hygiene. Hospital-acquired infections result in 3,000 Danes dying every year as well as in more than 1 million sick days, just as inadequate hygiene places an economic burden on society of close to DKK 4 billion. WHO (World Health Organization) estimates that in Europe alone, hospital-acquired infections result in a total of 16 million extra hospital days, 37,000 deaths and cost approximately EUR 7 billion (WHO). Hand hygiene is expected to be the main factor when it comes to hospital-acquired infections.

Today, many people have knowledge about correct hand hygiene practice, but the challenge remains to have this knowledge translated into changed behaviour. And it is not only with respect to the expensive hospital-acquired infections that good hand hygiene is important, since the effect of good hand hygiene has been documented in several other sectors.

Studies have e.g. shown that optimised focus on hand hygiene in day care facilities leads to significant reductions in the sickness absence among both children and staff as well as saves society large amounts in potential lost earnings, because parents do not have to take as many days off to take care of their sick children.

Data from interviews and focus groups and data from the technical measurements of lavatory user behaviour have already provided a clear indication that the hand hygiene habits associated with toilet visits of many patients are inadequate or virtually non-existent.

Under the auspices of the European Union, a set of recommendations were prepared in 2009 focusing on the prevention and control of healthcare-associated infections through education and training of healthcare personnel in respect of hygienic practice for controlling infections, through better dissemination of information to patients as well as through more research.

At present, no legislation dealing with this problem exists, which is presumably a consequence of the fact that no system exists for measuring and assessing the level of hygiene. Presently, conventional cleaning and control thereof is carried out on the basis of DS/INSTA 800 which is based on an assessment of visual cleanliness and not hygienic cleanliness. Consequently, the cleaning effort is generally not directed towards the non-visible illness-inducing microorganisms.

SUMMARY OF THE INVENTION

It is an object of the present invention to wholly or partly overcome the above disadvantages and drawbacks of the prior art. More specifically, it is an object to provide a system which promotes better hygiene behaviour among users of lavatories.

It is also an object to provide a system that may monitor hygiene behaviour of lavatory users and collect real-time data.

It is furthermore an object to provide a system that may monitor the state of lavatory components and their consumption and collect real-time data.

The above objects, together with numerous other objects, advantages, and features, which will become evident from the below description, are accomplished by a solution in accordance with the present invention by a hygiene behaviour support system for enhancing lavatory users' hand hygiene, comprising a lavatory comprising
    a toilet having a first sensor,
    a soap dispenser having a second sensor,
    a sink having a water tap, the water tap having a third sensor,
    a paper dispenser having a fourth sensor, and
    a disinfectant dispenser having a fifth sensor, and
a door through which a user can enter or leave the lavatory, the door having a closing mechanism,
wherein the disinfectant dispenser is connected with the closing mechanism of the door so that after a disinfectant has been dispensed from the disinfectant dispenser, the door will open.

In one embodiment, the sensors may be adapted to detect motion. The sensors are preferably comprised in the dispensers, water tap, and/or toilet. However, they may also be arranged in connection with the dispensers, water tap, and/or toilet.

Moreover, a passive infrared (PIR) sensor may be arranged in the lavatory.

Further, the PIR sensor may be arranged in a ceiling of the lavatory to detect movement of a person in the lavatory.

Also, a second PIR sensor may be arranged in the lavatory and may be directed towards the toilet and a zone around the toilet, the second PIR sensor being adapted to detect movement while a person is in the zone around the toilet.

Moreover, the toilet, the dispensers and the water tap may be adapted to be activated touch-free, i.e. a user may activate them without having to touch it, for instance by activating the sensor.

A button may be arranged in the vicinity of the door, the button being adapted to unlock the closing mechanism when being pushed.

Also, a touch-free mishap button may be arranged in the lavatory, the touch-free mishap button being adapted to close off the lavatory, if the lavatory has been contaminated.

In an embodiment, the toilet may comprise an automatic flush system.

Furthermore, a flush sensor may be arranged in a cistern of the toilet.

In addition, the sensors may be connected with a control unit.

Said sensors and the control unit may be wirelessly connected or connected by wire.

Moreover, the control unit may record observations received from the sensors. For instance, the control unit may also record registrations of certain behavourial scenarios of lavatory users.

In one embodiment of the hygiene behaviour support system, indicators may be arranged in connection with the soap dispenser, the water tap, the paper dispenser and the disinfectant dispenser, respectively.

Said indicators may be visible, such as light or illumination, or audible, such as a sound or a vibration.

Also, the control unit may, on the basis of the observations made by the sensors, control the indicators.

Further, the control unit may start the indicator arranged at the soap dispenser when the first sensor has been activated, the control unit may start the indicator at the water tap when the second sensor has been activated, the control unit may start the indicator at the paper dispenser when the third sensor has been activated, and the control unit may start the indicator at the disinfectant dispenser when the fourth sensor has been activated.

Moreover, the control unit may start the indicator arranged at the water tap when the first sensor has been activated, the control unit may start the indicator at the soap dispenser when the third sensor has been activated, the control unit may start the indicator at the water tap when the second sensor has been activated, the control unit may start the indicator at the paper dispenser when the third sensor has been activated, and the control unit may start the indicator at the disinfectant dispenser when the fourth sensor has been activated.

The control unit may be adapted to stop an indicator subsequent to it having started another indicator.

Additionally, the PIR sensor may be adapted to first detect a person entering the lavatory, and when the second PIR sensor detects movements of persons in the zone around the toilet, the second PIR sensor may be adapted to communicate this observation to the control unit.

The control unit may start the indicator arranged at the soap dispenser and/or the indicator arranged at the water tap when the second PIR sensor detects movements of persons in the zone around the toilet.

Further, the PIR sensor may be adapted to communicate to the control unit when for a predetermined time no movements of persons in the lavatory have been detected, whereby the control unit stops the indicators.

Additionally, the fifth sensor may detect when the disinfectant has been dispensed whereby the closing mechanism of the door is unlocked and the door is opened.

Also, the door may open automatically when the fifth sensor has detected that disinfectant has been dispensed from the disinfectant dispenser.

Moreover, the door may comprise an actuator adapted to open the door when the closing mechanism of the door is unlocked.

Furthermore, the disinfectant dispenser and the closing mechanism of the door may be wirelessly connected or connected by wire.

In addition, a storage unit may be arranged for storing data and observations from the sensors. The storage unit may be a database.

Also, a communication unit may be arranged for communicating the data and observations from the sensors.

Furthermore, the control unit may be monitoring the consumption of the dispensers.

In one embodiment, a second disinfectant dispenser may be arranged near the toilet.

Also, a guideline to the hygiene behaviour support system may be arranged at the door.

Said guideline may be shown on a poster or a sticker placed on a wall, a door or on a display.

The door may be a sliding door.

Furthermore, an actuator may be arranged in connection with the door, the actuator being adapted to open and close the door.

Also, a door sensor may be arranged outside the door, enabling touch-free opening of the door.

Moreover, a light panel may be arranged outside the door, indicating whether the lavatory is vacant, occupied or closed for service.

The storage unit may be adapted to receive data from biological and/or microbiological measurements performed in the lavatory.

The control unit may be adapted to close off the lavatory when the biological and/or microbiological measurements are exceeding a predetermined threshold.

The present invention also relates to a building comprising the hygiene behaviour support system as described above. Said building may be a hospital.

Further, the present invention relates to use of the hygiene behaviour support system as described above for hospitals, day care centres, schools, institutions, public buildings, pharmaceutical companies, the food industry, restaurants, offices etc.

Finally, the present invention relates to a method for enhancing lavatory users' hand hygiene, comprising the steps of
  detecting a user in the lavatory, and
  motivating the user to at least use disinfectant before leaving the lavatory by opening the door to the lavatory after a disinfectant has been dispensed from a disinfectant dispenser.

The method described above may further comprise the steps of
  guiding the user from the toilet to the soap dispenser by activating an indicator arranged at the soap dispenser after the toilet has flushed,
  guiding the user from the soap dispenser to the water tap by activating an indicator arranged at the water tap after the soap dispenser has dispensed soap,
  guiding the user from the water tap to the paper dispenser by activating an indicator arranged at the paper dispenser after the water tap has been activated, and
  guiding the user from the paper dispenser to the disinfectant dispenser by activating an indicator arranged at the disinfectant dispenser after the paper dispenser has been activated.

The step of detecting a person in the method as described above may be performed by a passive infrared (PIR) sensor.

BRIEF DESCRIPTION OF THE DRAWINGS

The invention and its many advantages will be described in more detail below with reference to the accompanying schematic drawings, which for the purpose of illustration show some non-limiting embodiments and in which.

All the figures are highly schematic and not necessarily to scale, and they show only those parts which are necessary in order to elucidate the invention, other parts being omitted or merely suggested.

DETAILED DESCRIPTION OF THE INVENTION

Figure 1:
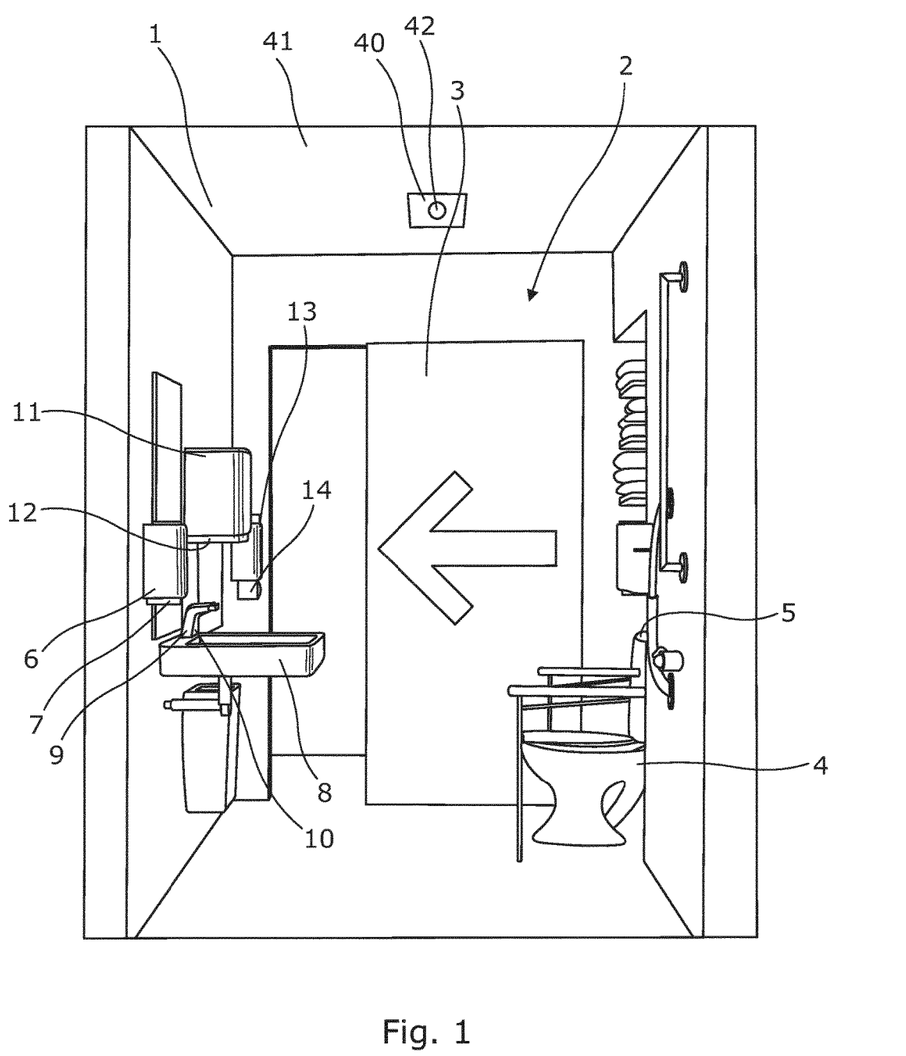
FIG. 1 shows a lavatory of a hygiene behaviour support system according to the invention seen from the end of the lavatory room opposite the door.

FIG. 1 shows a lavatory 1 of a hygiene behaviour support system 2 according to the present invention seen from an opposite end of the door 3. The hygiene behaviour support system 2 is adapted to enhance a person's hand hygiene after a toilet visit. The hygiene behaviour support system 2 comprises a lavatory 1. Inside the lavatory 1, different toilet components are arranged. In this embodiment, the lavatory 1 comprises a toilet 4 having a first sensor 5, a soap dispenser 6 having a second sensor 7, a sink 8 having a water tap 9, the water tap 9 having a third sensor 10. The lavatory 1 further comprises a paper dispenser 11 having a fourth sensor 12, and a disinfectant dispenser 13 having a fifth sensor 14. The hygiene behaviour support system 2 also comprises a door 3 through which a person may enter or leave the lavatory 1, the door 3 having a closing mechanism (not shown). Furthermore, the disinfectant dispenser 13 is connected with the closing mechanism of the door 3 so that after a disinfectant has been dispensed from the disinfectant dispenser 13, the door 3 will open.

Figure 2:
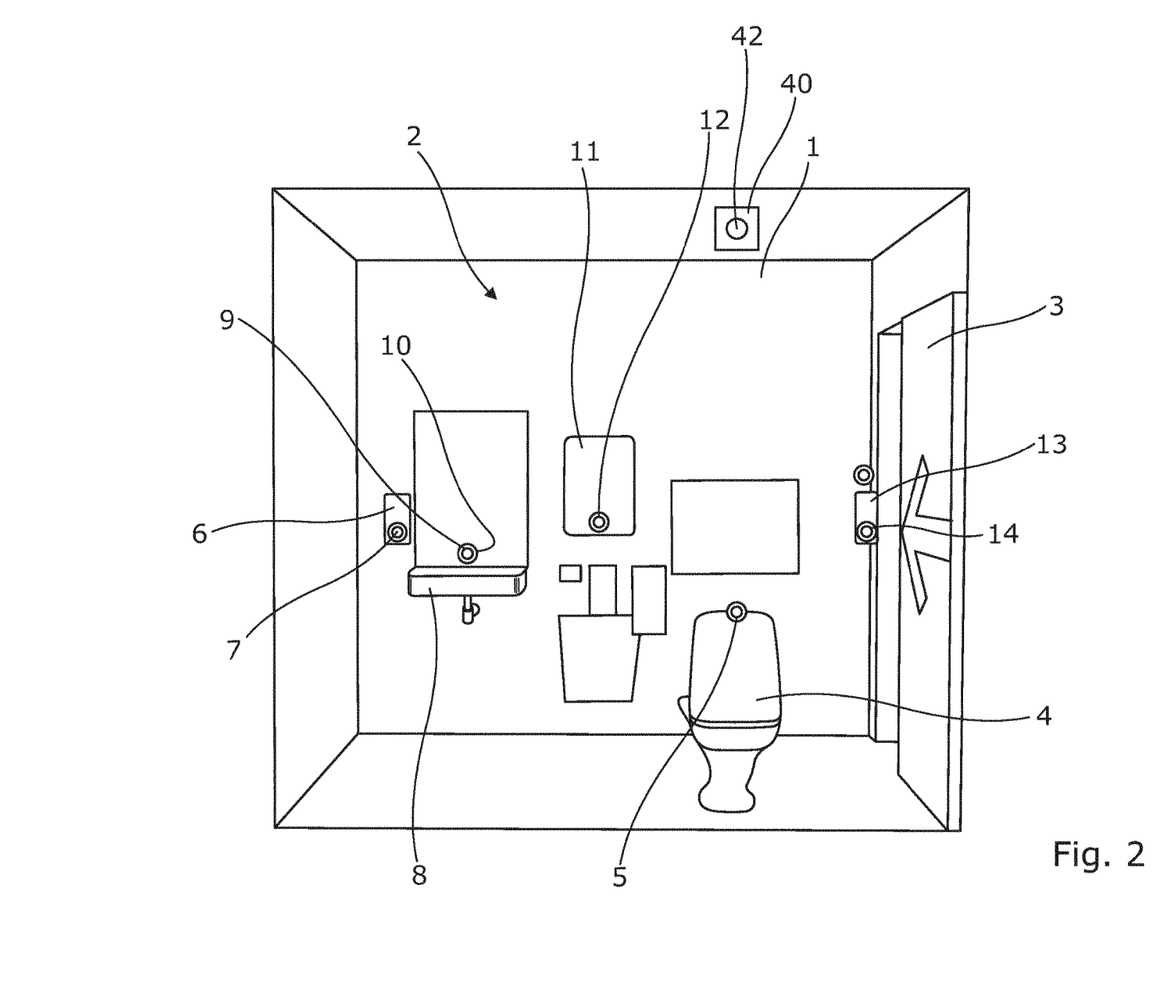
FIG. 2 shows the lavatory of FIG. 1 in another view.

Hereby it is obtained that the person having used the toilet and/or having been present in the lavatory is at least motivated to disinfect his/her hands before leaving the lavatory, since it is the disinfectant dispenser 13 which is adapted to open the door 3 when the fifth sensor 14 has detected that disinfectant has been dispensed. In FIG. 2, the lavatory 1 of FIG. 1 is shown in another view, wherein the toilet 4 is shown in a rear view, and the other components, the soap dispenser 6, the sink 8 and the paper dispenser 11 are shown in a front view. Furthermore, a passive infrared (PIR) sensor 40 is arranged in the lavatory 1. In this embodiment, the PIR sensor 40 is arranged in a ceiling 41 of the lavatory. The PIR sensor 40 is adapted to detect movement of persons inside the lavatory.

Furthermore, a second PIR sensor 42 is arranged in the lavatory and is directed towards the toilet and a zone around the toilet 4, the second PIR sensor 42 being adapted to detect movement while a person is in the zone around the toilet 4.

Advantageously, the toilet, the dispensers and the water tap may be touch-free, i.e. a user may activate said components without having to touch them.

Furthermore, indicators (not shown) may be arranged in connection with the soap dispenser, the water tap, the paper dispenser and the disinfectant dispenser, respectively. The indicators may be visible, such as light or illumination, or audible, such as a sound or a vibration. An embodiment of indicators will be described below.

The basic idea of the hygiene behaviour support system 2 is that users, by means of indicators, such as light, touch-free components and very simple written communication, is easily guided to good hand hygiene in connection with going to the lavatory. Further, the users will have their hands disinfected with a disinfectant, such as alcohol-based hand rub, before leaving the toilet lavatory 1, since the disinfectant dispenser 13 serves as a door opener.

Biological and microbiological measurements have shown that the surroundings in the lavatories 1 are contaminated and constitute a potential danger of contamination to the users. The hygiene behaviour support system makes it possible to use the lavatory without having to touch anything on the way in, during the visit and on the way out, presumably reducing the risk of infection.

The measurements made show that only approximately 10% of all visits to the toilet end by the user using spirits-based hand disinfectant. The direct coupling of exit from the toilet/lavatory with the use of a disinfectant will ensure that approximately 95% of toilet users will use spirits-based hand disinfectant (it is estimated that 5% will attempt to "trick" the system by either taking their hand away when the hand disinfectant is dispensed, or by using the emergency exit button).

Furthermore, the hygiene behaviour support system 2 is adapted to collect real-time measurements of the users' hygiene-related behavioural patterns when being in the lavatory 1. The hygiene behaviour support system 2 also comprises a control unit connected with the sensors. The data collected from the sensors are processed in a storage device, a database, and subsequently compared inter alia to a number of developed scenarios of user behaviour. On this basis, the hygiene behaviour support system 2 is capable of continuously defining the hygiene behaviour of each individual toilet visit, however always in anonymous form.

Also, the hygiene behaviour support system 2 is adapted to collect vital data from the various units of the system (soap dispenser, paper dispenser, disinfectant dispenser, water tap and toilet flush sensor). The collection of real-time data allows for the uptime of the hygiene behaviour support system 2—as compared to the uptime of non-monitored systems—to be considerably increased because the people responsible for the system are capable of monitoring and servicing the units before they run out of consumables and/or battery. Further, the maintenance of the system may—if desired—be placed with an external operator, and the servicing of the system may be planned in detail because of the close monitoring and data registration.

All of the above data collected on the storage device and/or server database, may be presented in display applications, hand-held units (iPads, tablets etc.) as well as on smartphones etc.

In connection with the data collection and intervention of the hygiene behaviour support system, SMS notifications or similar short messages may—in the long run—be sent to relevant persons, notifying them of desired intervention, for instance "There is no more spirits-based hand disinfectant of type X in dispenser Y in toilet Z" or "The ideal level of clean toilet visits in toilet X has been exceeded by Y %.

The hygiene behaviour support system 2 is based on a motivation mind-set and aims at involving the users in the maintenance of a correct hygiene standard and hence increasing their own health-related safety.

The display application developed is capable of displaying historical data about the hygiene behaviour exercised in the lavatories. As required, the various graphs present data hour by hour, day by day, month by month or the like and compare these data with e.g. the same data set from the day, month or year before. In this way, the user is involved directly and urged to "compete" with himself/herself in improving the hygiene level. The hospital may adopt desired levels as reference lines or the like, so everyone can see the desired level. It has never previously been possible to monitor the frequency of hand hygiene in real-time, and consequently it has never been possible to determine desired requirements in this respect. It is epoch-making that it is now possible to discuss the level of hand hygiene and then allow for qualified interventions in order to increase the focus on this area.

Display applications may also be used to show all types of hygiene-related information and guidance from hospital staff and staff responsible for hygiene.

In the case of alarming conditions such as the outbreak of for instance *E. Coli* or *Clostridium Difficile*, new guidelines for desired hygiene behaviour may be communicated via displays, and it may be measured directly whether the users embraces the new, strict guidelines. In other words, the hygiene behaviour support system 2 may form part of the crisis response and support the management by the staff of critical situations.

The hygiene behaviour support system 2 makes it possible for a user to be able to "close" the lavatory 1 for further visits, until the lavatory 1 has been cleaned, if the user believes that the lavatory 1 has been contaminated. The user has this opportunity both if the user finds the lavatory 1 contaminated when entering the lavatory 1, and if the user—due to his health/condition—contaminates the lavatory 1 himself (vomit, faeces or the like).

Again the user is involved in protecting himself and others from being infected with bacteria. A so-called "mishap button" (which is not a button but a touch-free sensor field) is envisaged, in front of which the user may place his hand for 5 seconds. If this is done, the lavatory will close so that it cannot be entered when this user has left, and the door will lock. The light panel by the door will flash orange—and it will say "service". The mishap button panel will also flash orange when this is activated. The service staff will be notified/called to clean the lavatory, e.g. by means of an SMS or an email saying e.g.: "Lavatory X in ward Y has just been closed down for service".

The server/database of the hygiene behaviour support system is prepared to be able to retrieve and process key data concerning the degree of cleanliness of the toilet by means of microbiological and biological measurements, etc.

As every lavatory is uniquely registered in the database, key data may be collected concerning other factors than hygiene behaviour and state of the units.

A method has been developed for defining the degree of cleanliness by means of systematic process control, which allows for the determination and control of a desired level of cleanliness.

Biological measurements have been used to define the degree of cleanliness, and these measurements have been performed by means of hand-held so-called ATP meters. Since these meters may send their data to a mac/PC via docking stations, it is possible to collect measurements of degrees of cleanliness before and after cleaning and process these data on the server of the hygiene behaviour support system.

A solution is being developed in which these data may be transferred wirelessly, and then an ecosystem may be established with hygiene behaviour and an ideal degree of cleanliness in the lavatory.

If either alarming hygiene behaviour and/or degrees of cleanliness are detected (these numbers may in the long term be compared and possibly anticipate alarming situations), the lavatory can be closed down and cleaning performed.

Figure 3:
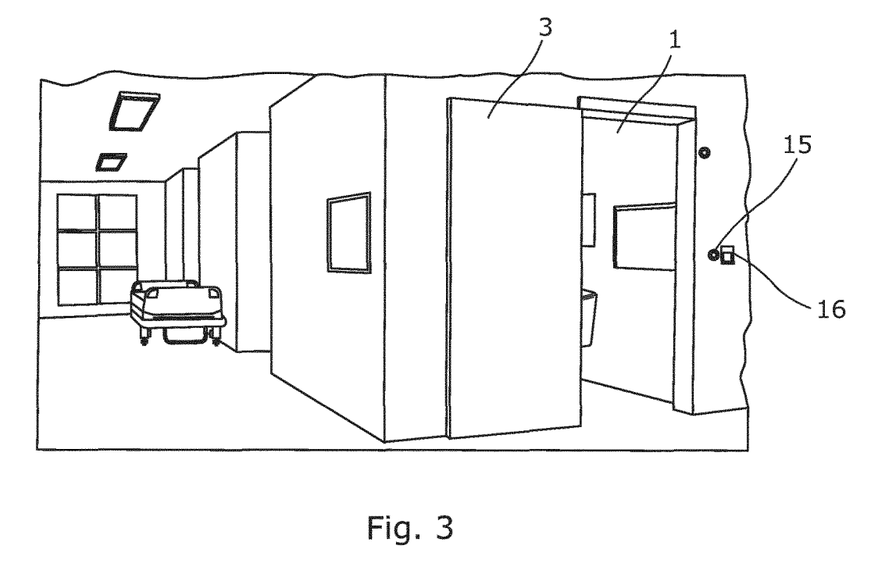
FIG. 3 shows the lavatory of FIG. 1 from the outside.

In FIG. 3, the lavatory 1 of FIG. 1 is shown from the outside. The door 3 is open and is, in this embodiment, a sliding door. An actuator (not shown) may be arranged in connection with the door 3, the actuator being adapted to open and close the door 3. Furthermore, a door sensor 15 is arranged outside the door 3, enabling touch-free opening of the door 3. A light panel 16 is arranged outside the door 3, indicating whether the lavatory 1 is vacant, occupied or closed for service. For instance, the light panel 16 may have a green light for when the lavatory is vacant, a red light for when the lavatory is occupied, and an orange light for when the lavatory is closed for service.

Figure 4:
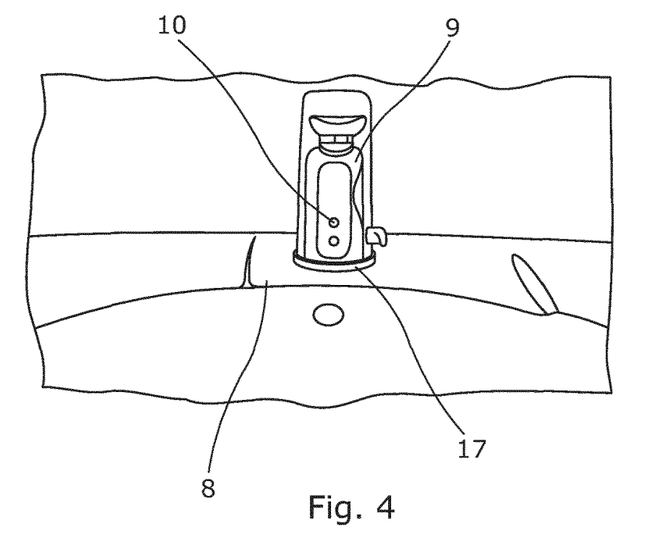
FIG. 4 shows a water tap.

In FIG. 4, an embodiment of a water tap 9 is shown. The water tap 9 has sensor 10 and an indicator 17. The indicator 17 is, in this embodiment, designed to be disc-shaped or ring-formed and is arranged below the water tap 9 and the sink 8. The disc-shaped indicator 17 comprises one or more light diodes arranged in the disc 17 so that the indicator 17 illuminates when the user is to be guided to the water tap 9. The disc 17 may be made of a fully or partly transparent material. The light diodes may be arranged inside the disc or they may be arranged in cavities in the disc. Preferably, the disc 17 and the light diodes may be adapted to withstand water from the sink and water tap. In another embodiment, the indicator to be arranged near the water tap may be arranged visibly on the wall behind or next to the water tap.

Figure 5:
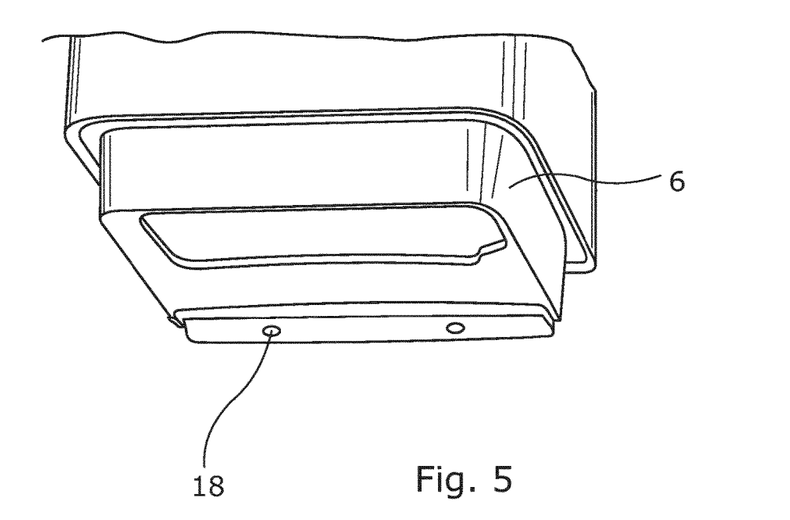
FIG. 5 shows a part of a soap dispenser.

FIG. 5 shows a part of a soap dispenser 7. An indicator 18, also here in the form of light diodes 18, is arranged on part of the soap dispenser 7.

Figure 6:
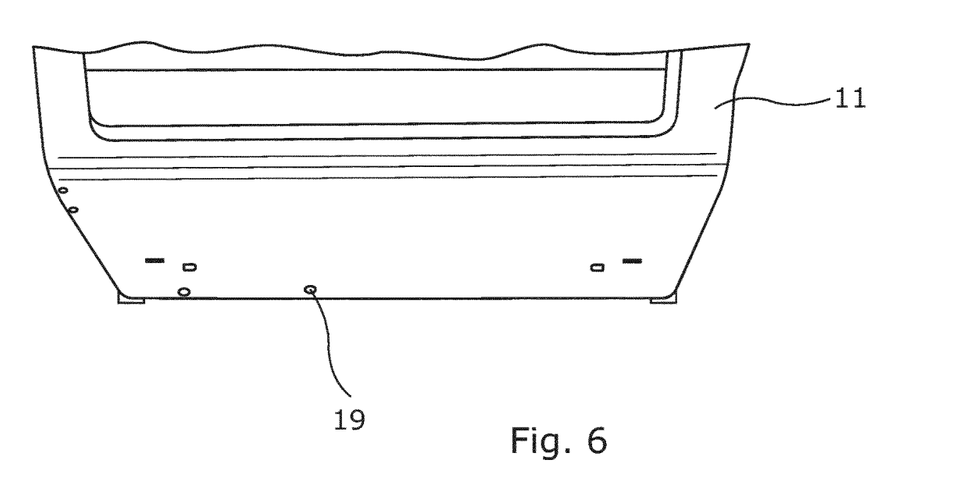
FIG. 6 shows a part of a paper dispenser.

FIG. 6 shows a part of a paper dispenser 11. An indicator 19, also here in the form of light diodes 19, is arranged on part of the paper dispenser 11.

The indicators, i.e. the light diodes 17, 18, 19, 22 have been incorporated directly into the soap dispenser 7, paper dispenser 11 and disinfectant dispenser 13, and in the case of the water tap 9, light diodes 17 are incorporated in close connection with the water tap 9. Whether the light guidance is directly incorporated into or placed in close connection with the unit is irrelevant in principle, as long as the light guidance illuminates the area around the unit.

At present, light guidance is preferred at hospitals since hospital staff does not desire the use of guiding by means of sound. However, sound guidance could be used in other contexts, either together with or without guiding by means of light.

Figure 7:
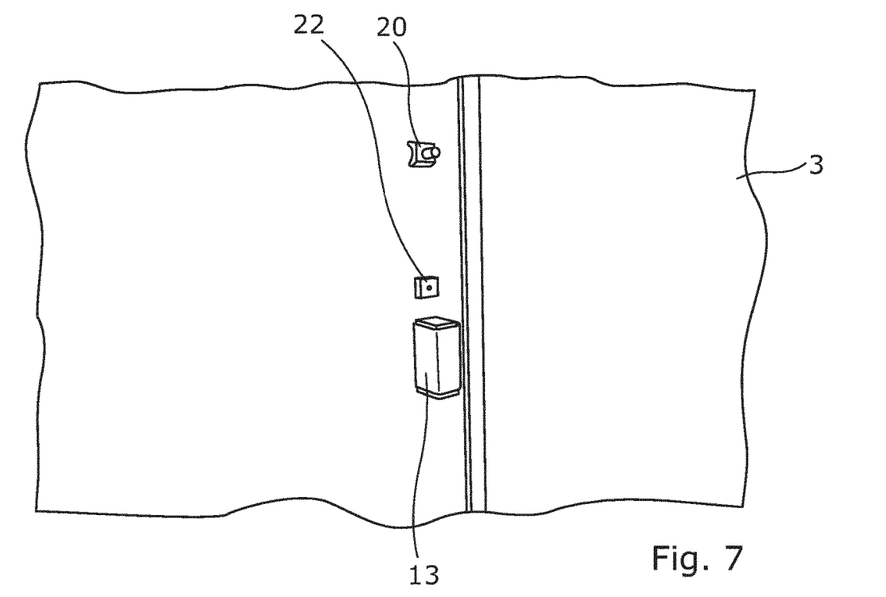
FIG. 7 shows the disinfectant dispenser and the door.

In FIG. 7, the disinfectant dispenser 13 is arranged at the door 3. According to the inventive idea, a sensor of the disinfectant dispenser detects when the disinfectant has been dispensed, whereby the closing mechanism of the door 3 is unlocked and the door 3 is being opened. Furthermore, a button 20 is arranged in the vicinity of the door 3, the button 20 being adapted to unlock the closing mechanism when being pushed, so that the door may be opened manually in case of an emergency. An indicator 22 is arranged in connection with the disinfectant dispenser 13.

Figure 8:
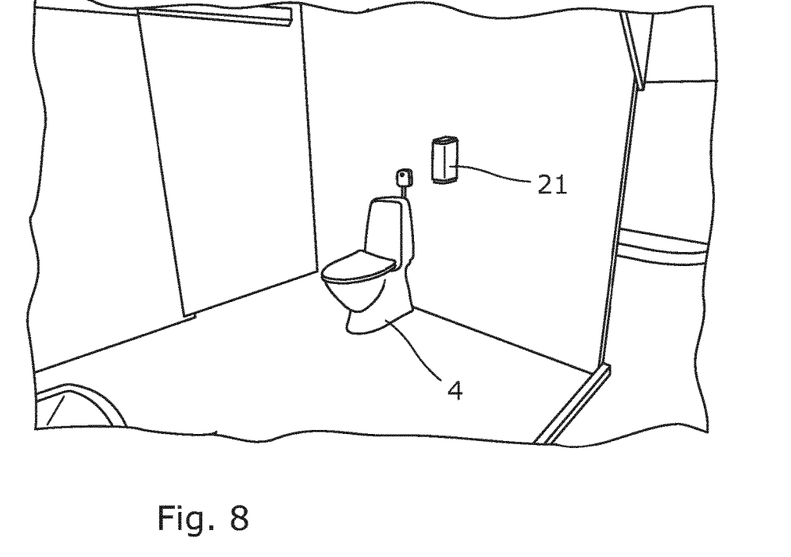
FIG. 8 shows the toilet and a second disinfectant dispenser.

In FIG. 8, a second disinfectant dispenser 21 may be arranged in the vicinity of the toilet 4 so that the user or caregiver or nurse may use this if necessary.

Preferably, the hygiene behaviour support system 2 comprises existing toilet elements known per se from modern lavatories—i.e. touch-free soap, hand disinfectant and paper dispensers and toilets with automatic flush.

Figure 9:
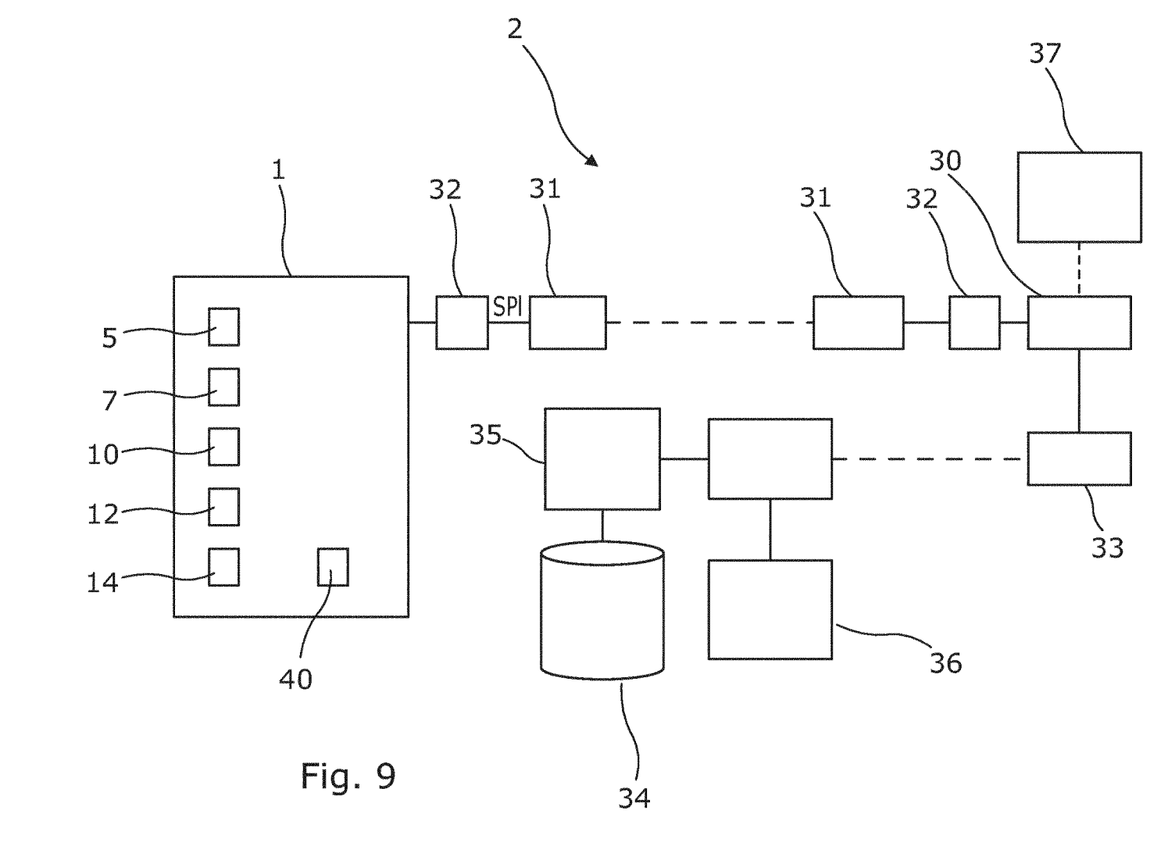
FIG. 9 shows schematically the hygiene behaviour support system.

In FIG. 9, a schematical view of the hygiene behaviour support system 2 is shown. The core of the hygiene behaviour support system 2 is the control unit 30, for instance a Netduino open source electronic platform based in a 32-bit microcontroller.

The Netduino 30 is a down-system connected with the toilet components, for instance the sensors 5, 7, 10, 12, 14, 40 in an embodiment via a central wireless transceiver 31, and then via a number of local, wireless transceivers 31 and PIC circuits 32 which are all installed directly in the soap, disinfectant and paper dispensers as well as by the water tap and the toilet flush sensor Furthermore, the soap, disinfectant and paper dispensers are all provided with newly developed LED light sources, i.e. indicators, which—by means of pulsating light in a certain order—guide the users to performing good hand hygiene. Current is supplied to the local transceivers 31, PIC circuits 32 and directly from the dispensers' own battery supply, and the extra current power consumption does not change the otherwise normal lifetime of the batteries.

The Netduino 30 is up-system connected via a wireless 3G modem 33 (connection may also be made via an existing Ethernet connection) to for instance a Windows Azure database solution 34, i.e. the storage unit 34, which is a heavy open source cloud-platform. The programming language is based on .Net and is handled via NHibernate module 35. The code is in the cloud, which allows for system maintenance and development to be performed decentrally. In another embodiment, the code is present on the Netduino 30 so the overall security of the system is enhanced. However, system maintenance and development are to be performed locally.

Real-time key data from the hygiene behaviour support system 2 may be presented directly in a—especially for the system—browser-developed display-user interface. Hence, data from the system may be delivered to a locally installed display 36 in a patient ward, on which to display information about the current hand hygiene. Information thus flows to the service provider responsible for replenishing consumables (soap, hand disinfectant, paper and batteries etc.) and to e.g. the hygiene units in the hospital being responsible for hygiene together with the heads of the various wards.

As all data about the state of consumables (paper, soap and hand disinfectant consumption) as well as the battery level of all the units are collected continuously, it is possible to prevent entirely that the units run out of battery/power or go out of operation. All data from the system may be passed on directly via an SMS service to the persons responsible for the cleaning of the lavatories and e.g. to the hygiene nurse in the event that the hand hygiene drops below the desired level Furthermore, biological and/or microbiological measurements may be used to define the degree of cleanliness, and these measurements have been performed by means of hand-held so-called ATP meters 37.

Introduction and guide to the hygiene behaviour support system 2:

1. The light panel outside the toilet door indicates whether the lavatory is occupied or vacant (red and green colour) or closed for service (orange colour).

2. The door is opened by sliding the hand past a black sensor field. The door opens.

3. The door closes and is automatically locked when the user has entered and is free of the door (having a sensor by the door prevents the user from getting stuck in the door).

4. The light panel outside the door now lights up red, meaning that the toilet lavatory is occupied.

5. The light panel inside the lavatory also lights up red, so that the user is made aware visually that the door is locked.

6. A graphic system overview is placed on the wall above or across the toilet (a sticker or poster) or on the door, or on a display, informing the user that the door is automatically locked, and that the toilet flushes automatically when the user moves away from the toilet, that light by the soap dispenser, water tap and paper dispenser will remind them to perform correct hand hygiene, and that the door is opened by means of the hand disinfectant dispenser.

7. The toilet flushes automatically when the patient moves away from the toilet—the user should not touch the sensor panel. If extra flush is desired, the user may move his hand past the toilet sensor and the toilet will flush again.

8. Light and soap (and possibly water tap) are activated in connection with toilet visits in order to motivate the users to perform good hand hygiene (the activation of the indicators may be started by the PIR sensors and/or the first sensor).

9. Soap is dispensed by the user placing his hand below the dispenser—the user should not touch the soap dispenser.

10. When soap is dispensed by the user, light by the water tap is turned on.

11. The water is turned on by the user placing his hands below the tap—the user should not touch the water tap.

12. The water is automatically turned off when the user removes his hands.

13. The paper dispenser lights up after use of water.

14. Paper is dispensed when the user places his hands below the paper dispenser—the user should not touch the dispenser.

15. The hand disinfectant dispenser is placed by the door and lights up when paper has been dispensed.

16. Hand disinfectant is dispensed by the user placing his hands below the dispenser—the user should not touch the dispenser. The activation of the hand disinfectant dispenser opens the door.

17. The door opens.

18. The door closes automatically again (the PIR sensor communicates to the control unit when for a predetermined time no movements of persons in the lavatory have been detected, whereby the control unit stops the indicators).

19. The light panel outside the door lights up green again. The toilet is vacant.

Although the invention has been described in the above in connection with preferred embodiments of the invention, it will be evident for a person skilled in the art that several modifications are conceivable without departing from the invention as defined by the following claims.

The invention claimed is:

1. A hygiene behaviour support system for enhancing a person's hand hygiene after a toilet visit, comprising:
 a lavatory comprising:
   a toilet having a first sensor,
   a soap dispenser having a second sensor,
   a sink having a water tap, the water tap having a third sensor,
   a paper dispenser having a fourth sensor, and
   a disinfectant dispenser having a fifth sensor, and
 a door through which a person can enter or leave the lavatory, the door having a closing mechanism,
 wherein the disinfectant dispenser is connected with the closing mechanism of the door so that after a disinfectant has been dispensed from the disinfectant dispenser, the door will open,
 wherein each sensor is connected with a control unit,
 wherein the control unit, on the basis of the observations made by each sensor, controls indicators, and
 wherein the control unit starts an indicator arranged at the soap dispenser when the first sensor has been activated, the control unit starts an indicator at the water tap when the second sensor has been activated, the control unit starts an indicator at the paper dispenser when the third sensor has been activated, and the control unit starts an indicator at the disinfectant dispenser when the fourth sensor has been activated.

2. A hygiene behaviour support system according to claim 1, wherein the sensors are adapted to detect motion.

3. A hygiene behaviour support system according to claim 1, wherein a passive infrared (PIR) sensor is arranged in the lavatory.

4. A hygiene behaviour support system according to claim 3, wherein the PIR sensor is arranged in a ceiling of the lavatory to detect movement of a person in the lavatory.

5. A hygiene behaviour support system according to claim 3, wherein a second PIR sensor is arranged in the lavatory and is directed towards the toilet and a zone around the toilet, the second PIR sensor being adapted to detect movement while a person is in the zone around the toilet.

6. A hygiene behaviour support system according to claim 1, wherein the control unit records observations received from the sensors.

7. A hygiene behaviour support system according to claim 1, wherein indicators are arranged in connection with the soap dispenser, the water tap, the paper dispenser and the disinfectant dispenser, respectively.

8. A hygiene behaviour support system according to claim 1, wherein the control unit starts the indicator arranged at the water tap when the first sensor has been activated, the control unit starts the indicator at the soap dispenser when the third sensor has been activated, the control unit starts the indicator at the water tap when the second sensor has been activated, the control unit starts the indicator at the paper dispenser when the third sensor has been activated, and the control unit starts the indicator at the disinfectant dispenser when the fourth sensor has been activated.

9. A hygiene behaviour support system according to claim 1, wherein the control unit is adapted to stop an indicator subsequent to it having started another indicator.

10. A hygiene behaviour support system according to claim 3, wherein the PIR sensor is adapted to first detect a person entering the lavatory, and when a second PIR sensor detects movements of persons in a zone around the toilet, the second PIR sensor is adapted to communicate this observation to the control unit.

11. A hygiene behaviour support system according to claim 3, wherein the control unit starts the indicator arranged at the soap dispenser and/or the indicator arranged at the water tap when the second PIR sensor detects movements of persons in a zone around the toilet.

12. A hygiene behaviour support system according to claim 7, wherein the PIR sensor is adapted to communicate to the control unit when for a predetermined time no movements of persons in the lavatory have been detected, whereby the control unit stops the indicators.

13. A hygiene behaviour support system according to claim 1, wherein the fifth sensor detects when the disinfectant has been dispensed whereby the closing mechanism of the door is unlocked and the door is opened.

14. A hygiene behaviour support system according to claim 13, wherein the door opens automatically when the fifth sensor has detected that disinfectant has been dispensed from the disinfectant dispenser.

15. A hygiene behaviour support system according to claim 1, wherein a storage unit is arranged for storing data and observations from the sensors.

16. A computer implemented method for enhancing a person's hand hygiene during a toilet visit, the method comprising:
detecting a person in a lavatory,
guiding the person from a toilet to a soap dispenser by activating an indicator arranged at the soap dispenser,
guiding the person from the soap dispenser to a water tap by activating an indicator arranged at the water tap after the soap dispenser has dispensed soap,
guiding the person from the water tap to a paper dispenser by activating an indicator arranged at the paper dispenser after the water tap has been activated,
guiding the person from the paper dispenser to the disinfectant dispenser by activating an indicator arranged at the disinfectant dispenser after the paper dispenser has been activated, and
wherein activation of the indicators is controlled by the computer.

17. A method according to claim 16 further comprising motivating the person to at least use disinfectant before leaving the lavatory by opening a door to the lavatory after a disinfectant has been dispensed from a disinfectant dispenser.

18. A hygiene behaviour support system for enhancing a person's hand hygiene after a toilet visit, comprising:
a lavatory comprising:
a toilet having a first sensor,
a soap dispenser having a second sensor,
a sink having a water tap, the water tap having a third sensor,
a paper dispenser having a fourth sensor, and
a disinfectant dispenser having a fifth sensor, and
a door through which a person can enter or leave the lavatory, the door having a closing mechanism,
wherein the disinfectant dispenser is connected with the closing mechanism of the door so that after a disinfectant has been dispensed from the disinfectant dispenser, the door will open,
wherein each sensor is connected with a control unit,
wherein the control unit, on the basis of the observations made by each sensor, controls indicators, and
wherein the control unit starts an indicator arranged at the water tap when the first sensor has been activated, the control unit starts an indicator at the soap dispenser when the third sensor has been activated, the control unit starts an indicator at the water tap when the second sensor has been activated, the control unit starts an indicator at the paper dispenser when the third sensor has been activated, and the control unit starts an indicator at the disinfectant dispenser when the fourth sensor has been activated.

19. A hygiene behaviour support system for enhancing a person's hand hygiene after a toilet visit, comprising:
an indicator configured for arranging at a soap dispenser to guide the person from the toilet to the soap dispenser after a first sensor detects that the person has been in a zone around the toilet;
an indicator configured for arranging at a water tap to guide the person from the soap dispenser to the water tap after the soap dispenser has dispensed soap;
an indicator configured for arranging at a paper dispenser to guide the person from the water tap to the paper dispenser after the water tap has been activated;
an indicator configured for arranging at a disinfectant dispenser to guide the person from the paper dispenser to the disinfectant dispenser after the paper dispenser has been activated; and
a controller programmed to control activation of each indicator.

20. A hygiene behaviour support system according to claim 19, wherein each indicator is visible by light or illumination.

21. A hygiene behaviour support system according to claim 19, wherein a second sensor detects that the soap dispenser has dispensed soap, a third sensor detects that the water tap has been activated and a fourth sensor detects that the paper dispenser has been activated.

22. A hygiene behaviour support system according to claim 19, wherein each sensor is adapted to detect motion.

23. A hygiene behaviour support system according to claim 19, wherein the controller records observations received from each sensor.

24. A hygiene behaviour support system according to claim 19 further comprising a passive infrared (PIR) sensor configured to detect movement of a person.

25. A hygiene behaviour support system according to claim 1, wherein each indicator is visible by light or illumination.

26. A method according to claim 16, wherein each indicator is visible by light or illumination.

27. A hygiene behaviour support system according to claim 18, wherein each indicator is visible by light or illumination.

* * * * *